US008460921B2

(12) United States Patent (10) Patent No.: US 8,460,921 B2
Gross (45) Date of Patent: Jun. 11, 2013

(54) MULTINETWORK NERVE CELL ASSAY PLATFORM WITH PARALLEL RECORDING CAPABILITY

(75) Inventor: Guenter W. Gross, Denton, TX (US)

(73) Assignee: University of North Texas, Denton, TX (US)

( * ) Notice: Subject to any disclaimer, the term of this patent is extended or adjusted under 35 U.S.C. 154(b) by 867 days.

(21) Appl. No.: 12/441,703

(22) PCT Filed: Sep. 12, 2007

(86) PCT No.: PCT/US2007/019780
§ 371 (c)(1),
(2), (4) Date: Jul. 20, 2009

(87) PCT Pub. No.: WO2008/100287
PCT Pub. Date: Aug. 21, 2008

(65) Prior Publication Data
US 2009/0291466 A1 Nov. 26, 2009

Related U.S. Application Data

(60) Provisional application No. 60/845,399, filed on Sep. 18, 2006.

(51) Int. Cl.
*C12M 1/34* (2006.01)
(52) U.S. Cl.
USPC .......... 435/287.1; 435/29; 435/285.2; 607/50
(58) Field of Classification Search
USPC ..... 435/29, 285.2, 287.1, 4, 7.2, 368; 607/50, 607/117, 118
See application file for complete search history.

(56) References Cited

U.S. PATENT DOCUMENTS

2002/0025573 A1* 2/2002 Maher et al. ............... 435/287.1
2006/0173259 A1* 8/2006 Flaherty et al. ............... 600/331
2006/0194255 A1* 8/2006 Finkel ........................... 435/7.1

OTHER PUBLICATIONS

Gramowski, Schiffmann and Gross, "Quantification of acute neurotoxic effects of trimethyltin using neuronal networks cultured on microelectrode arrays," NeuroToxicology, 21:331-42, 2000.
Gross and Gopal, Emerging histiotypic properties of cultured neuronal networks. In: M. Taketani and M. Baudry (eds) Advances in Network Electrophysiology using Multi-Electrode Arrays. Springer, pp. 193-214. 2006.
Gross and Pancrazio Neuronal Network Biosensors. In: Smart Biosensor Technology (G.K. Knopf and A.S. Bassi, eds), Taylor and Francis Publishers, CRC Press.pp. 177-201, 2006.

(Continued)

*Primary Examiner* — Michael Hobbs
(74) *Attorney, Agent, or Firm* — Jackson Walker L.L.P.

(57) ABSTRACT

A neuronal network analysis plate having alternating rows of recording wells and amplifying wells. The recording wells contain a neural cell network and a series of electrodes for recording the action potential signals of the neurons. The electrodes are connected to amplifiers in adjacent amplifying wells. The close proximity of these amplifiers ideal because it permits the parallel, non-multiplexed recording of action potential signals from multiple different active nerve cell networks. The amplifiers in the amplifying wells can then be connected to external amplification equipment. The neuronal network analysis plate may be contained within a single commercially available 24 or 96 well plate. The neuronal network analysis plate can be used to detect and quantify pharmacological and toxicological responses of the neural cells to one or more agents in vitro.

11 Claims, 3 Drawing Sheets

OTHER PUBLICATIONS

Gross, Rieske, Kreutzberg and Meyer, "A new fixed-array multimicroelectrode system designed for longterm monitoring of extracellular single unit neuronal activity in vitro," Neurosci. Lett., 6:101-05, 1977.

Gross, "Internal dynamics of randomized mammalian neuronal networks in culture," In:Enabling Technologies for Cultured Neural Networks, Stenger and McKenna (Eds.), Academic Press, NY, pp. 277-317, 1994.

Gross, Harsch, Rhoades and Gopel, "Odor, drug, and toxin analysis with neuronal networks in vitro: extracellular array recording of network responses," Biosensors and Bioelectronics, 12:373-93, 1997.

Keefer, Gramowski and Gross, "NMDA receptor dependent periodic oscillations in cultured spinal cord networks," J. Neurophysiol., 86:3030-3042, 2001a.

Keefer, Gramowski, Stenger, Pancrazio and Gross, "Characterization of acute neurotoxic effects of trimethylolpropane phosphate via neuronal network biosensors," Biosensors and Bioelectronics 16: 513-52, 2001b.

Meyer, Jochen F., et al., Magnetic Stimulation and Depression of Mammalian Networks in Primary Neuronal Cell Cultures, In Press, pp. 1-10.

Shafer, T.J., Complete Inhibition of Spontaneous Activity in Neuronal Networks in Vitro by Deltamethrin and Permethrin, Neurotoxicology, vol. 29, 2008, pp. 203-212.

Keefer, Edward W., Carbon Nanotube Coating Improves Neuronal Recordings, NatureNanotechnology, vol. 3, Jul. 2008, pp. 434-439.

* cited by examiner

A.

B.

MULTINETWORK NERVE CELL ASSAY PLATFORM WITH PARALLEL RECORDING CAPABILITY

This application claims priority to U.S. Provisional Patent Application Ser. No. 60/845,399, entitled "Multinetwork Nerve Cell Assay Platform With Parallel Recording Capability," filed on Sep. 18, 2006, the entire content of which is hereby incorporated by reference.

The United States government has certain rights in the present invention pursuant to grant number N66001-00-C-8024 (SPAWAR/ONR) from the DARPA.

BACKGROUND

This invention pertains to neural networks, and particularly to multinetwork, multielectrode assay devices capable of completely parallel, non-multiplexed recording of action potential signals.

In the last decade, substantial and crucial progress has been made in the validation of primary neuronal cell cultures as pharmacological research platforms. Networks in culture are spontaneously active and produce action potential (AP) patterns that change in a predictable and reproducible manner in response to physical and chemical/pharmacological perturbations of their environment. By growing such networks on arrays of substrate integrated microelectrodes (Gross et al., 1977; Gross 1994), intimate contact with the electrodes can be achieved, providing high signal-to-noise ratios, long-term stability, and an operational lifetime of several months. The monitoring of many nerve cells in such networks yields rich spatio-temporal patterns, subtle sup-population responses, and general fault tolerance, as all data analysis is based on nerve cell groups rather than single neurons. Realistic applications to the fields of toxicology, pharmacology, and drug development are emerging (Gross et al., 1997; Morefield et al., 2000; Gramowski et al., 2000; Keefer et al., 2001a,b, Gross and Gopal, 2006).

It also has been shown that such networks function as biosensors, as they respond to any compound that can alter the normal function of the nervous system and do not require a-priori knowledge (or "fingerprints") of the agents encountered (Gross et al., 1997, Gross and Pancrazio, 2006). They represent "broad-band" biosensors of interest to the military and homeland security. A stand-alone automated sensor station prototype already exists at the Naval Research Laboratory (NRL/UNT collaboration under DARPA Activities Detection Program). As complex, spontaneously active systems, the networks also embody the mystery of pattern generation, processing, and storage, and therewith, the initial steps and strategies of information processing.

Two-network arrays for simultaneous recording from two separate networks (32 electrodes each) are now in routine use at select institutions. However, this approach is still far from what is needed for efficient exploration and applications of network dynamics. Statistical evaluations of interculture repeatability, multiple drug and sequential concentration applications, and of the temporal evolution of toxic responses are tedious and far too slow for present industrial and even research requirements.

A major temporal and financial burden associated with drug development and toxicology assessment is the lack of physiological assay platforms that are positioned between the biochemist and the animal or human experiments in order to provide rapid, quantitative data on neuroactive/neurotoxic responses. What is lacking in the art is a platform that uses the complex and sensitive neurophysiological network dynamics (provided by the simultaneous recording of action potentials from hundreds of nerve cells), for determination of pharmacological and toxicological responses. By employing many networks in parallel in an automated, robotic system, it would be highly desirable to develop a highly-efficient screening of compounds that would substantially accelerate research in these areas, and drastically reduce the number of animals required by present testing and evaluation procedures. The central nervous system tissue from embryos of one pregnant mouse (usually 10-12) can produce cell pools that allow the seeding of over 1000 networks. This represents an extraordinary efficiency in tissue utilization.

SUMMARY

The present invention relates generally to the field of neuronal networks. In particular, this invention relates to multinetwork, multiwell assay plates having alternating columns for cell culture and for the recording circuitry. These assay plates allow the parallel, non-multiplexed recording of action potential signals from numerous active nerve cell networks simultaneously.

Generally, the current invention provides devices employing highly-sensitive neurophysiological network dynamics to detect and quantitate a variety of pharmacological and toxicological responses in vitro. The multiwell, multielectrode assay devices have a minimum of at least 2 separate neural networks per plate, each of these networks being served by a number of microelectrodes sufficient to allow a statistical description of major changes in network activity patterns. Depending on the size of the network, this can range from ten to several hundred. As an example, a 3 mm diameter planar network can be monitored effectively by 32 microelectrodes. Pluralities of two or more such networks may be arranged in tandem, in parallel, or in series within a given system to be served by the robot. One or more recording stations may preferably be included with the sample platform of the robotic liquid handling system allowing simultaneous recording from numerous networks before and during their exposure to pharmacological agents.

The signals collected by the microelectrodes are passed first to "insertion" VSLI or miniaturized preamplifiers. The closer the preamplifier or first stage preamplification circuitry is to the electrode, the better. This reduces noise and is optimal for microvolt recording. In some embodiments, the preamplifiers can be added to one or more sides of the multinetwork plate to provide the action potential data recorded extracellularly from each electrode. The current invention utilizes tried and proven passive thin film microelectrode leads coupled to VLSI operational amplifiers. Other solutions use discontinuous laser scanning methods that have not been proven to work and cause loss of data inherent to the scanning procedure.

The current invention is particularly advantageous because it utilizes, within a single assay plate, alternating columns of wells for cell culture and for the recording and amplification circuitry. Each column of wells in the plate containing cultured cells is immediately adjacent to a column of wells containing respective recording circuitry. Thus, the preamplifier circuitry is within 10-20 mm of the recording electrodes. The use of an industry standardized 24 or 96 well plate is ideal because it permits the parallel, non-multiplexed recording from up to 48 active nerve cell networks. This is also convenient due to the ease of obtaining these plates. Any standardized well plate could be used with any desired number of nerve cell networks. The use of glass plates and transparent indium-tin oxide ("ITO") conductors also permits optical evaluation of network health via phase contrast microscopy and the use of fluorescence techniques. The use of glass plates with passive conductors, but without integrated amplification circuitry on the plate, drastically reduces fabrication costs and allows sterilization via autoclaving. The methodology requires primarily mature nerve cell networks (achieved 3 to 4 weeks after the initial seeding of cells). Therefore, many such multi-array plates must be used to provide a continuous supply of networks for routine assays and analyses. It is essential to make these plates as simple, rugged, and cheap as possible.

DETAILED DESCRIPTION OF PREFERRED EMBODIMENTS

The present invention relates to neuronal networks useful for detecting and quantitating pharmacological and toxicological responses in vitro. In particular, the present invention pertains to a 48-network analysis plate with amplification circuitry in an adapted commercial 96-well format.

One aspect of the present invention is a neuronal network analysis plate that utilizes a commercially available 24 or 96 well assay plate. The network analysis plate includes alternating rows of wells dedicated to either (a) cell culture and recording or (b) connection and amplification. For the exemplary 96 well plate, each row of 8 wells dedicated to cell culture and containing the electrodes and recording equipment is immediately adjacent to a row of 8 wells that contains respective connection and amplification equipment. The amplification equipment included in each amplification well preferably includes two VLSI amplifiers. Thus, the first stage signal amplification takes place within 8-10 mm of the electrode recording craters. An eight well bus bar contacts the top of each amplification well and carries the amplified signal to connectors for second stage amplification.

Figure 1:
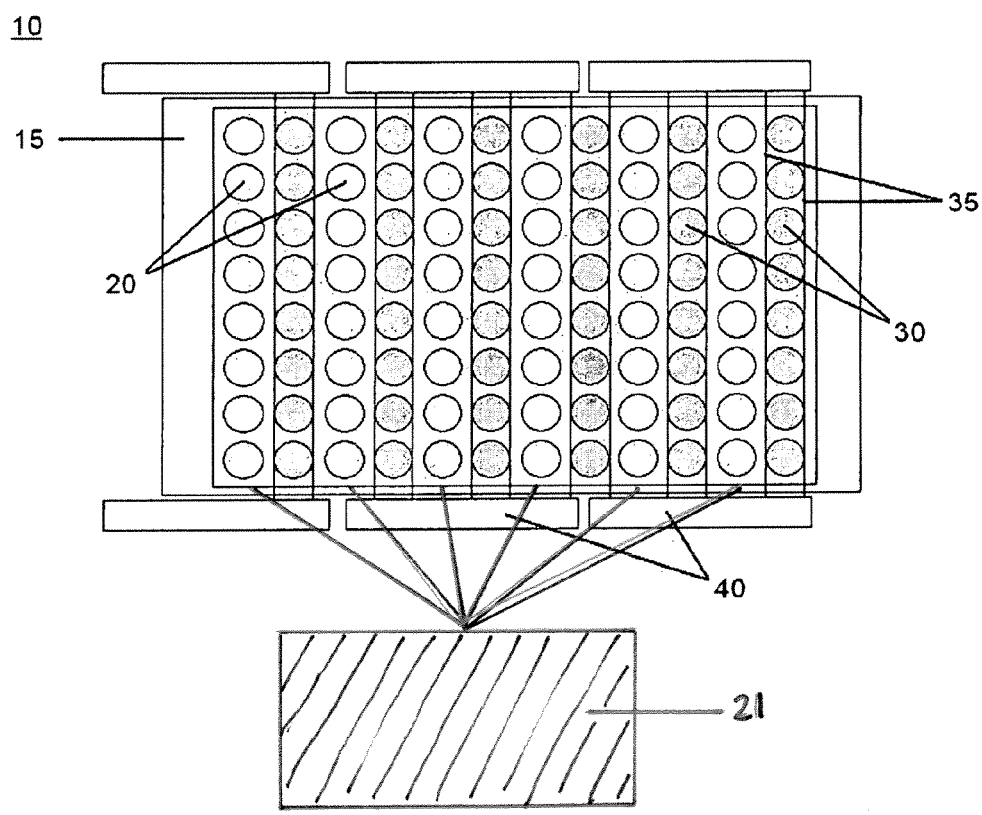
FIG. 1 shows a top view of one embodiment, a 48-network analysis plate utilizing a commercially available 96 well assay plate.

With regard to FIG. 1, an embodiment of a network analysis plate 10 is illustrated. The network analysis plate 10 utilizes a standard 96 well assay plate 15. The network analysis plate 10 contains alternating rows of recording wells 20 and amplifying wells 30. The amplifying wells 30 are contacted by bus bars 35 which carry the amplified signals to the connectors 40. The connectors 40 then carry the amplified signals to the second stage amplification equipment.

The recording wells 20 contain viable nerve cell networks. The nerve cell networks themselves can be prepared in an expert cell culture lab and shipped to the final location to be used for experiments. At the origin, the networks should receive a quality control check that includes morphological and electrophysiological evaluations. The latter will provide a settings file that contains the location of discriminated active units, their signal to noise ratios, and the network firing pattern. This file can be opened at the destination for immediate evaluation of the product after shipping. The nerve cell networks in the open wells are preferably maintained by a robotic platform 21 which is responsible for maintaining osmolarity, feeding, and medium changes, as well as the application of test compounds. The activity of the neuronal network is monitored by a series of electrodes. Preferably, thirty-two (32) electrodes are used with the nerve cell network contained within the recording well 20.

With reference to FIG. 2A, a recording well 20 is shown adjacent to an amplifying well 30. Within recording well 20 is the neural cell network 22 that is interspersed with electrodes for recording the action potential signals. Within amplifying well 30 are thirty-two gold pads 27 that serve as contacts. With reference to FIG. 2B, a 32-line interconnect 25 is shown which connects the electrodes from the neural cell network 22 to each of the gold pads 27 in the amplifying well 30. With reference to FIG. 2C, the amplifying well 30 is shown to have two VLSI amplifiers 32. The gold pads 27 at the bottom of the amplifying well 30 make contact with the VLSI amplifiers 32, which then make contact with the upper contact pads 34. The upper contact pads 34 then make contact with the bus bars 35 shown in FIG. 1. As discussed above, the bus bars 35 carry the amplified signals to the connectors 40, as shown in FIG. 1, which then carry the amplified signals to any preferred second stage amplification equipment.

Figure 2:
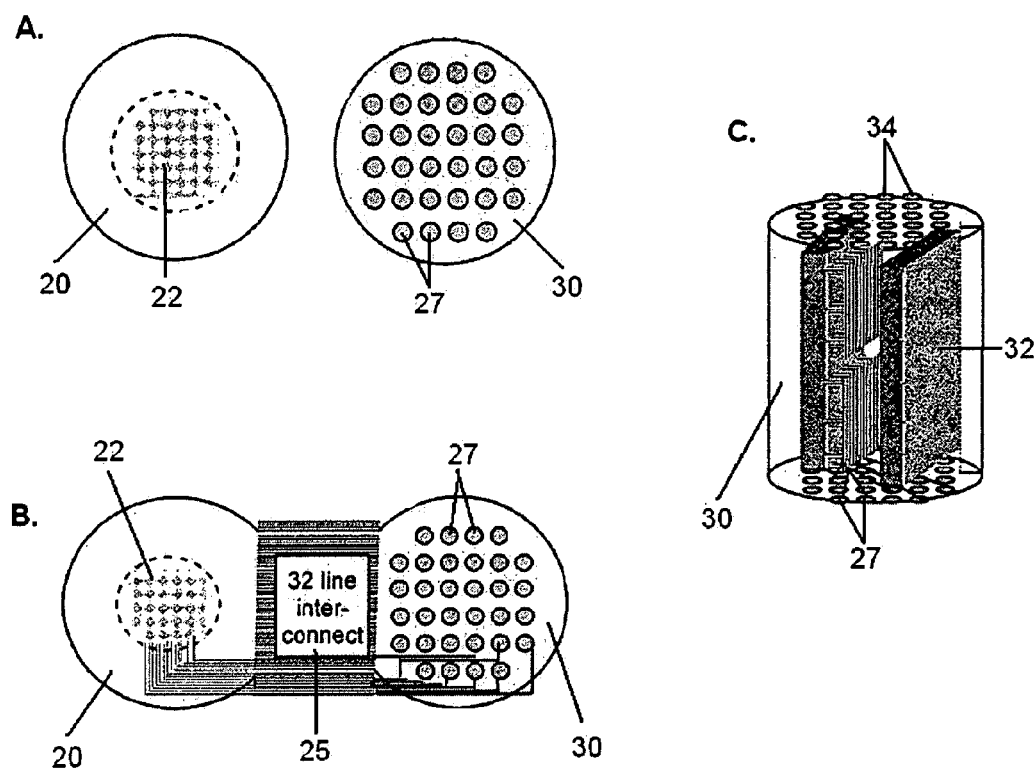
FIG. 2A shows a top view of an embodiment of a recording well adjacent to an amplification well.
FIG. 2B shows a top view of an embodiment of a recording well adjacent to an amplification well and having an interconnect passing between the two wells.
FIG. 2C shows a side view of an embodiment of an amplification well with "insertion" VLSI preamplifiers.

Preferably, the VLSI amplifiers 32 shown in FIG. 2 are 16 channel VLSI amplifiers that are capable of fitting within a cylindrical well that is 6 mm in diameter and 10 mm tall.

Figure 3:
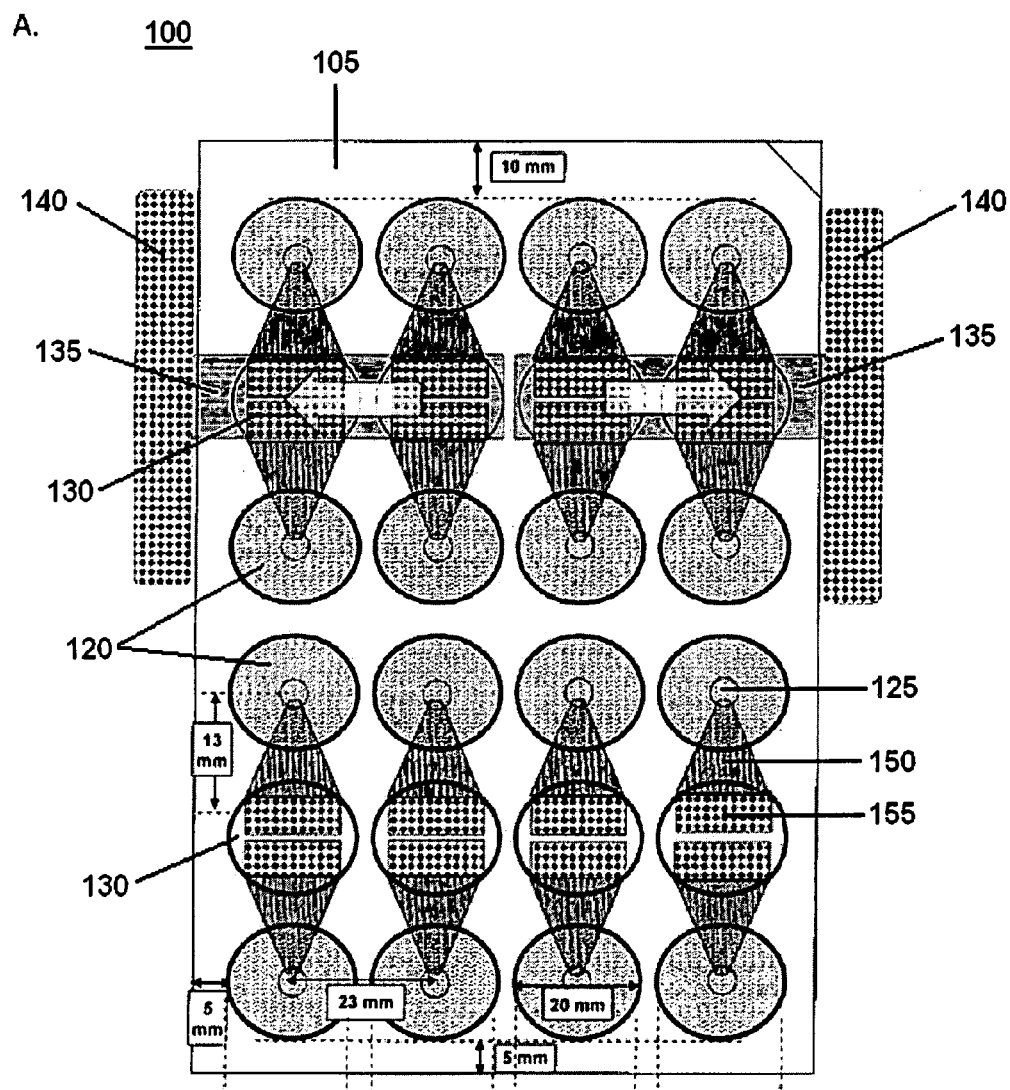
FIG. 3A shows a top view of one embodiment, a 16-network analysis plate utilizing a commercially available 24 well assay plate, with exemplary measurements.
FIG. 3B shows a side view of an embodiment of a network analysis plate, with exemplary measurements.
Figure 3:
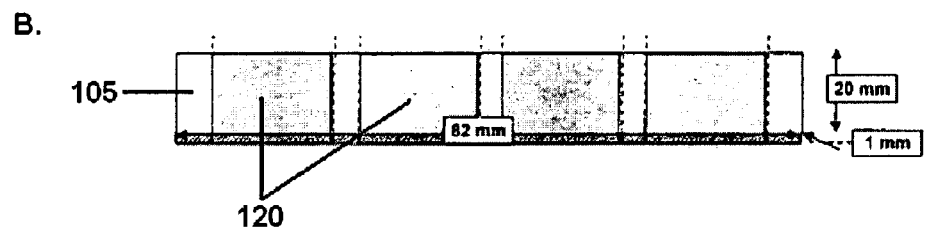

With regard to FIG. 3A, an alternate embodiment of a network analysis plate 100 is illustrated, with exemplary measurements between components. The network analysis plate 100 utilizes a standard 24 well assay plate 105 having a 16 network platform. The network analysis plate 100 contains alternating rows of recording wells 120 and amplifying wells 130. The amplifying wells 130 are contacted by bus bars or bus lines 135, which are preferably 128 Ch and include power. The bus lines 135 carry the amplified signals to the connectors 140. The arrows illustrated in FIG. 3A superimposed on the bus lines 135 show the direction in which the signals pass to the connectors 140. The recording wells 120 contain viable nerve cell networks. The network recording area 125 is preferably in the center of the recording well 120. A set of 32 thin film conductors 150 connect the electrodes in the network recording areas 125 to the amplifying wells 130. The amplifying wells 130 are shown to contain two analog preamplifiers 155 each.

FIG. 3A illustrates a side view of an embodiment of a network analysis plate utilizing a standard 24 well assay plate 105. Exemplary measurements are shown, particularly with regard to the recording wells 120.

One preferred embodiment of the present invention is a neuronal network analysis plate comprising a plurality of recording wells organized into a plurality of recording rows. Each recording well contains a neural cell network and a plurality of electrodes for recording signals from the neural cell network. The neuronal network analysis plate also comprises a plurality of amplifying wells organized into a plurality of amplifying rows. Each amplifying well contains one or more amplifiers for amplifying recording signals from the recording wells. The plurality of recording rows and the plurality of amplifying rows are alternating such that each recording well is adjacent to a corresponding amplifying well. The neuronal network analysis plate also comprises a plurality of interconnects. Each interconnect connects the electrodes of a recording well with the amplifiers of a corresponding amplifying well.

In additional preferred embodiments, the plurality of recording wells in the neuronal network analysis plate can comprise 48 recording wells organized into 6 recording rows and the plurality of amplifying wells can comprise 48 amplifying wells organized into 6 amplifying rows. Alternatively, the neuronal network analysis plate utilizes the wells of a standard 96 well plate having 12 rows of 8 wells each. The neuronal network analysis plate can also comprise 16 recording wells organized into 4 recording rows and 8 amplifying wells organized into 2 amplifying rows. This neuronal network analysis plate may utilize the wells of a standard 24 well plate having 6 rows of 4 wells each. In a further preferred embodiment, the neuronal network analysis plate further comprises a plurality of bus bars in contact with the amplifiers in the amplifying wells. The bus bars can be connected to connectors, and the connectors can be connected to secondary amplification equipment. The neuronal network analysis plate can also further comprise a robotic liquid handling system that is capable of interacting with the plate to maintain osmolarity in the wells, feed and change the medium in the recording wells to maintain the neural cell networks, and apply any test compounds.

A further preferred embodiment is a method for parallel, non-multiplexed recording of action potential signals from active nerve cell networks exposed to one or more agents. The method comprises first preparing an embodiment of the neuronal network analysis plate, then exposing the recording wells of the neuronal network analysis plate to the agents, and finally recording the signals that are amplified by the amplifying wells of the neuronal network analysis plate. Alternatively, if secondary amplification equipment is used, the final step can involve recording the signals amplified by the secondary amplification equipment. The agents can be pharmacological agents or any test compounds.

A further preferred embodiment is a method for detecting and quantifying pharmacological and toxicological responses of neural cells to one or more agents in vitro. The method comprises first preparing an embodiment of the neuronal network analysis plate, then exposing the recording wells of the neuronal network analysis plate to the agents, and finally recording the signals that are amplified by the amplifying wells of the neuronal network analysis plate. Alternatively, if secondary amplification equipment is used, the final step can involve recording the signals amplified by the secondary amplification equipment. Also, the final step can involve the analysis of the recorded signals, which allows the user to quantify the pharmacological and toxicological responses of the neural cells to the one or more agents. A person of skill in the art would understand how to analyze and compare recorded action potential signals to better understand the pharmacological and toxicological response of a neural cell network to different agents. The agents can be pharmacological agents or any test compounds.

REFERENCES CITED

The following U.S. Patent documents and publications are hereby incorporated by reference.

Other Publications

Gramowski, Schiffmann and Gross, "Quantification of acute neurotoxic effects of trimethyltin using neuronal networks cultured on microelectrode arrays," *NeuroToxicology*, 21:331-42, 2000.

Gross and Gopal, Emerging histiotypic properties of cultured neuronal networks. In: M. Taketani and M. Baudry (eds) Advances in Network Electrophysiology using Multi-Electrode Arrays. Springer, pp 193-214. 2006.

Gross and Pancrazio Neuronal Network Biosensors. In: Smart Biosensor Technology (G. K. Knopf and A. S. Bassi, eds), Taylor and Francis Publishers, CRC Press. pp 177-201, 2006.

Gross, Rieske, Kreutzberg and Meyer, "A new fixed-array multimicroelectrode system designed for longterm monitoring of extracellular single unit neuronal activity in vitro," *Neurosci. Lett.*, 6:101-05, 1977.

Gross, "Internal dynamics of randomized mammalian neuronal networks in culture," In: Enabling Technologies for Cultured Neural Networks, Stenger and McKenna (Eds.), Academic Press, NY, pp. 277-317, 1994.

Gross, Harsch, Rhoades and Gopel, "Odor, drug, and toxin analysis with neuronal networks in vitro: extracellular array recording of network responses," *Biosensors and Bioelectronics,* 12:373-93, 1997.

Keefer, Gramowski and Gross, "NMDA receptor dependent periodic oscillations in cultured spinal cord networks," *J. Neurophysiol.*, 86:3030-3042, 2001a.

Keefer, Gramowski, Stenger, Pancrazio and Gross, "Characterization of acute neurotoxic effects of trimethylolpropane phosphate via neuronal network biosensors," *Biosensors and Bioelectronics* 16: 513-52, 2001b.

What is claimed is:

1. A neuronal network analysis plate comprising:

a plurality of recording wells organized into a plurality of recording rows, wherein each recording well contains a neural cell network and a plurality of electrodes for recording action potential signals from the neural cell network;

a plurality of amplifying wells organized into a plurality of amplifying rows, wherein each amplifying well contains one or more miniaturized, insertion VLSI preamplifiers inserted fully into each amplifying well for amplifying recording signals from the recording wells, wherein the plurality of recording rows and the plurality of amplifying rows are alternating such that each recording well is adjacent to a corresponding amplifying well, wherein the miniaturized, insertion VLSI preamplifiers are located within about 10 to about 20 mm of the plurality of electrodes, wherein the miniaturized, insertion VLSI preamplifiers are capable of fitting within a cylindrical well about 6 mm in diameter and about 10 mm tall, and wherein the miniaturized, insertion VLSI preamplifiers comprise a plurality of contact pads for connection to the plurality of electrodes;

a plurality of interconnects, wherein each interconnect connects the electrodes of a recording well with the plurality of contact pads of the miniaturized, insertion VLSI preamplifiers of a corresponding amplifying well; and secondary amplification equipment connected to the miniaturized, insertion VLSI preamplifiers.

2. The neuronal network analysis plate of claim 1, wherein the plurality of recording wells comprises 48 recording wells organized into 6 recording rows, and wherein the plurality of amplifying wells comprises 48 amplifying wells organized into 6 amplifying rows.

3. The neuronal network analysis plate of claim 2, wherein the neuronal network analysis plate utilizes the wells of a standard 96 well plate having 12 rows of 8 wells each.

4. The neuronal network analysis plate of claim 1, wherein the plurality of recording wells comprises 16 recording wells organized into 4 recording rows, and wherein the plurality of amplifying wells comprises 8 amplifying wells organized into 2 amplifying rows.

5. The neuronal network analysis plate of claim 4, wherein the neuronal network analysis plate utilizes the wells of a standard 24 well plate having 6 rows of 4 wells each.

6. The neuronal network analysis plate of claim 1, wherein the miniaturized, insertion VLSI preamplifiers further comprise upper contact pads, and further comprising a plurality of bus bars in contact with the upper contact pads of the miniaturized, insertion VLSI preamplifiers in the amplifying wells.

7. The neuronal network analysis plate of claim 6, wherein the bus bars are connected to connectors, and wherein the connectors are connected to the secondary amplification equipment.

8. The neuronal network analysis plate of claim 1, further comprising:
 a robotic liquid handling system capable of interacting with the plate to maintain osmolarity in the recording wells of the plate, add medium to the recording wells of the plate, or apply test compounds to the recording wells of the plate.

9. A method for parallel, non-multiplexed recording of action potential signals from active nerve cell networks exposed to one or more agents, comprising:
 preparing the neuronal network analysis plate of claim 1;
 exposing the recording wells of the neuronal network analysis plate to the one or more agents; and
 recording the signals amplified by the amplifying wells of the neuronal network analysis plate.

10. The method of claim 9, wherein the one or more agents are one or more pharmacological agents.

11. A method for parallel, non-multiplexed recording of action potential signals from active nerve cell networks exposed to one or more agents, comprising:
 preparing the neuronal network analysis plate of claim 7;
 exposing the recording wells of the neuronal network analysis plate to the one or more agents; and
 recording the signals amplified by the secondary amplification equipment.

* * * * *